United States Patent
Stellon et al.

(10) Patent No.: US 6,319,266 B1
(45) Date of Patent: Nov. 20, 2001

(54) TROCAR SYSTEM AND METHOD OF USE

(75) Inventors: Gene Stellon, Southington; David C. Racenet, Southbury; Ralph A. Stearns, Bozrah; Adam Lehman, Wallingford, all of CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/526,837

(22) Filed: Mar. 16, 2000

(51) Int. Cl.[7] ................................................ A61B 17/34
(52) U.S. Cl. ........................... 606/185; 604/164.01
(58) Field of Search ................................ 606/185, 181, 606/170, 167, 108, 158; 604/164.01–164.04

(56) References Cited

U.S. PATENT DOCUMENTS

| | | |
|---|---|---|
| 4,535,773 | 8/1985 | Yoon . |
| 4,601,710 | 7/1986 | Moll . |
| 4,654,030 | 3/1987 | Moll et al. . |
| 4,902,280 | 2/1990 | Lander . |
| 4,931,042 | 6/1990 | Holmes et al. . |
| 5,030,206 | 7/1991 | Lander . |
| 5,066,288 | 11/1991 | Deniega et al. . |
| 5,104,382 | 4/1992 | Brinkerhoff et al. . |
| 5,114,407 | 5/1992 | Burbank . |
| 5,116,353 | 5/1992 | Green . |
| 5,152,754 | 10/1992 | Plyley et al. . |
| 5,158,552 | 10/1992 | Borgia et al. . |
| 5,226,426 | 7/1993 | Yoon . |
| 5,246,425 | 9/1993 | Hunsberger et al. . |
| 5,275,583 | 1/1994 | Crainich . |
| 5,290,243 | 3/1994 | Chodorow et al. . |
| 5,295,993 | 3/1994 | Green . |
| 5,312,354 | 5/1994 | Allen et al. . |
| 5,314,417 | 5/1994 | Stephens et al. . |
| 5,318,580 | 6/1994 | Gresl, Jr. . |
| 5,318,585 | 6/1994 | Guy et al. . |
| 5,346,459 | 9/1994 | Allen . |
| 5,356,421 | 10/1994 | Castro . |
| 5,364,365 | 11/1994 | Wortrich . |
| 5,387,197 | 2/1995 | Smith et al. . |
| 5,411,515 | 5/1995 | Haber et al. . |
| 5,417,705 | 5/1995 | Haber et al. . |
| 5,474,539 | 12/1995 | Costa et al. . |
| 5,486,190 | 1/1996 | Green . |
| 5,522,833 | 6/1996 | Stephens et al. . |
| 5,527,335 | 6/1996 | Bolduc et al. . |
| 5,538,509 | 7/1996 | Dunlap et al. . |
| 5,674,237 | 10/1997 | Ott . |
| 5,676,156 | 10/1997 | Yoon . |
| 5,697,947 | 12/1997 | Wolf et al. . |
| 5,851,216 | * 12/1998 | Allen ........................... 604/164.01 |
| 5,868,773 | 2/1999 | Danks et al. . |
| 5,904,699 | * 5/1999 | Schwemberger et al. ........... 606/185 |
| 5,984,941 | 11/1999 | Wilson et al. . |

FOREIGN PATENT DOCUMENTS

| | | |
|---|---|---|
| 0 604 197 A2 | 12/1993 | (EP) . |
| 0 617 924 A2 | 2/1994 | (EP) . |
| WO 94/22508 | 3/1994 | (WO) . |

* cited by examiner

*Primary Examiner*—Kevin Truong

(57) ABSTRACT

A trocar system including a cannula and an obturator assembly being at least partially insertable through the cannula. The obturator assembly including a housing, a penetrating tip disposed at a distal end, an elongated shield including a guard extending from a shaft are movable relative to the penetrating tip, and a latch mechanism disposed generally within the housing. The latch mechanism facilitates changing the configuration of the obturator assembly between a fixed-shield orientation, wherein at least a portion of the guard is maintained to extend at least partially distal of the penetrating tip to prevent puncturing of tissue by the penetrating tip, to a non-fixed shield orientation whereby upon application of force to the distal end of the obturator assembly, the guard and penetrating tip are permitted to move relative one another to facilitate puncturing of tissue by the penetrating tip.

9 Claims, 13 Drawing Sheets

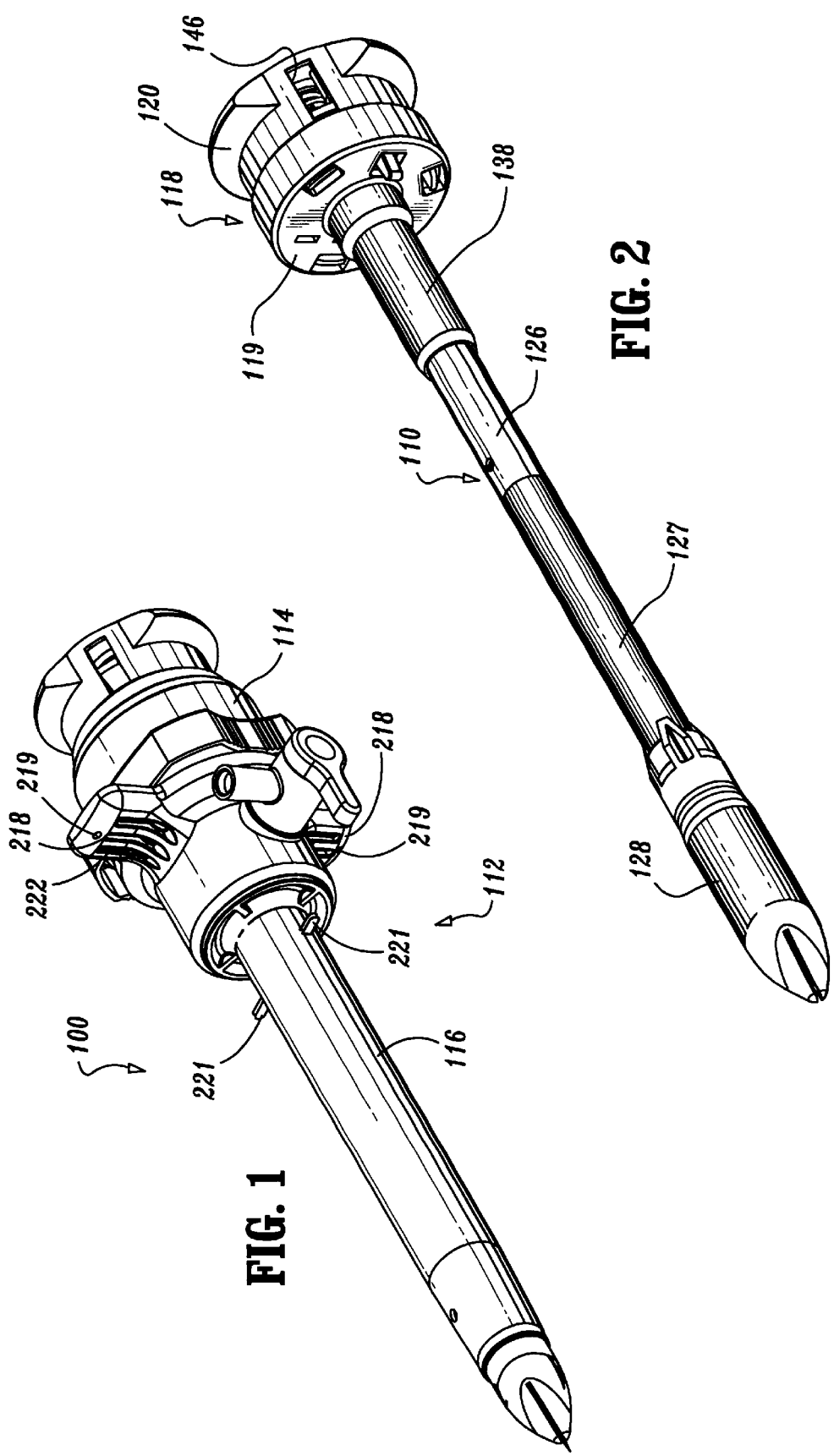

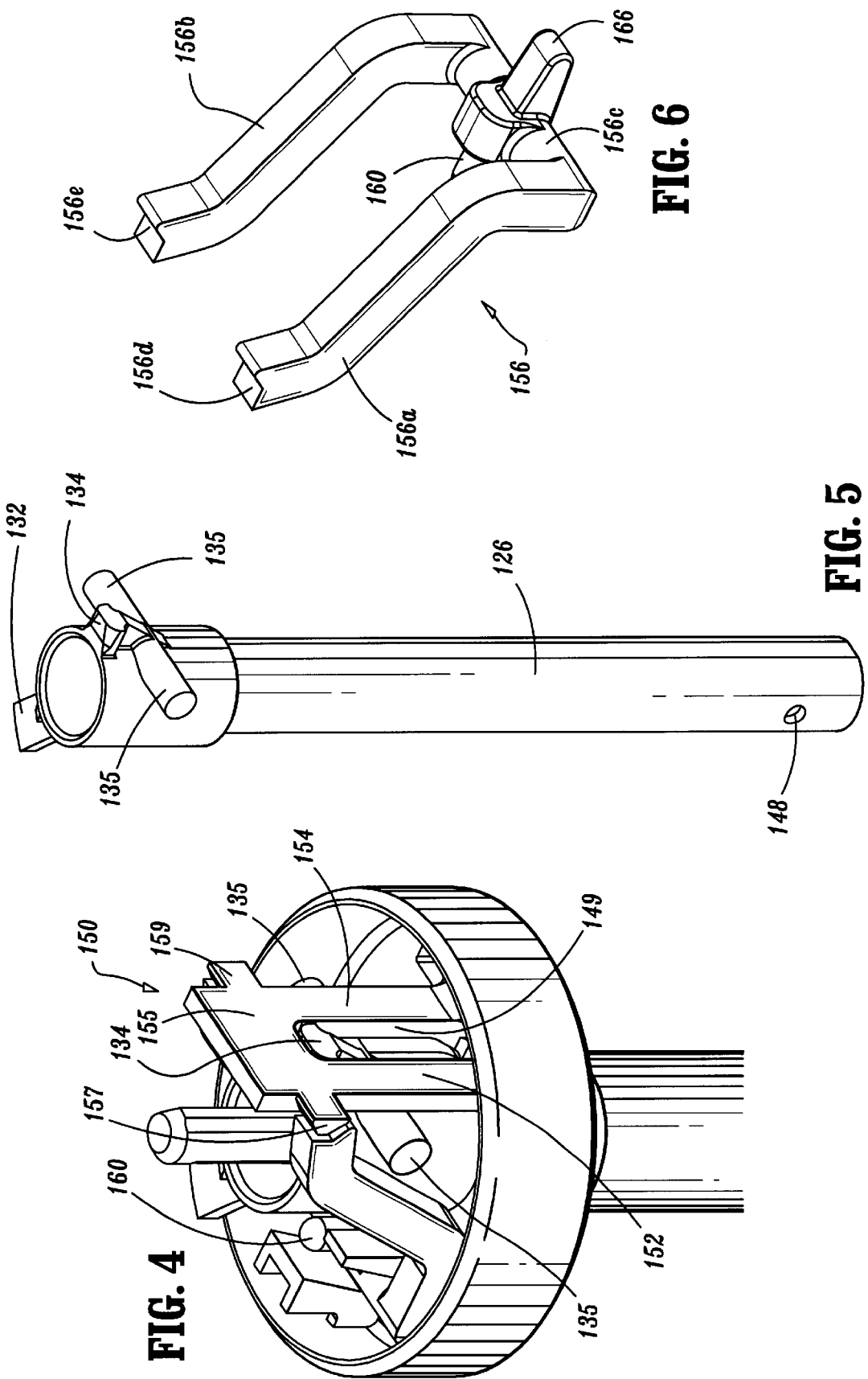

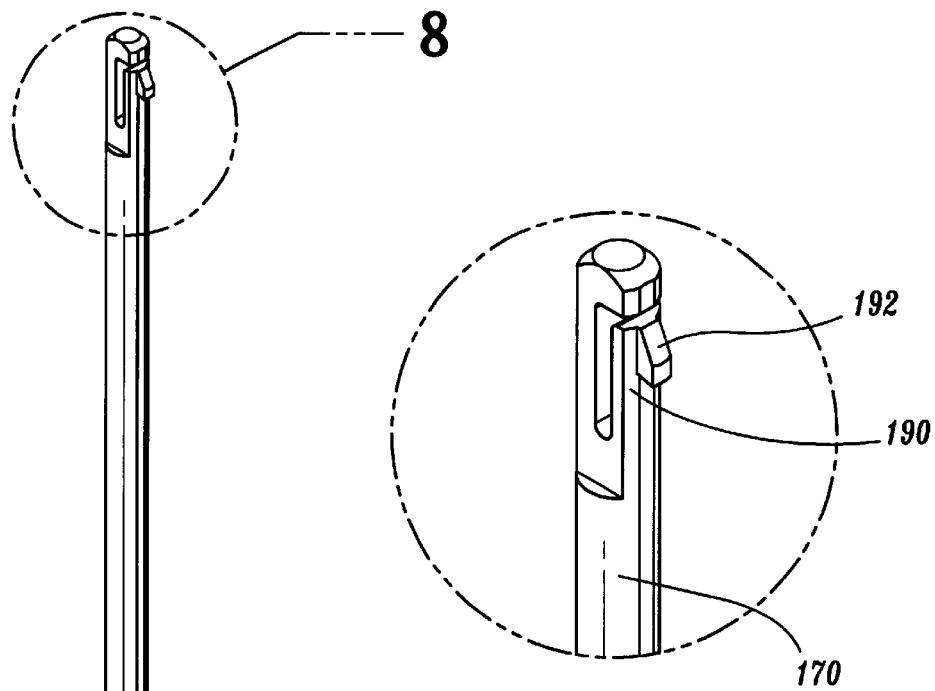
FIG. 8
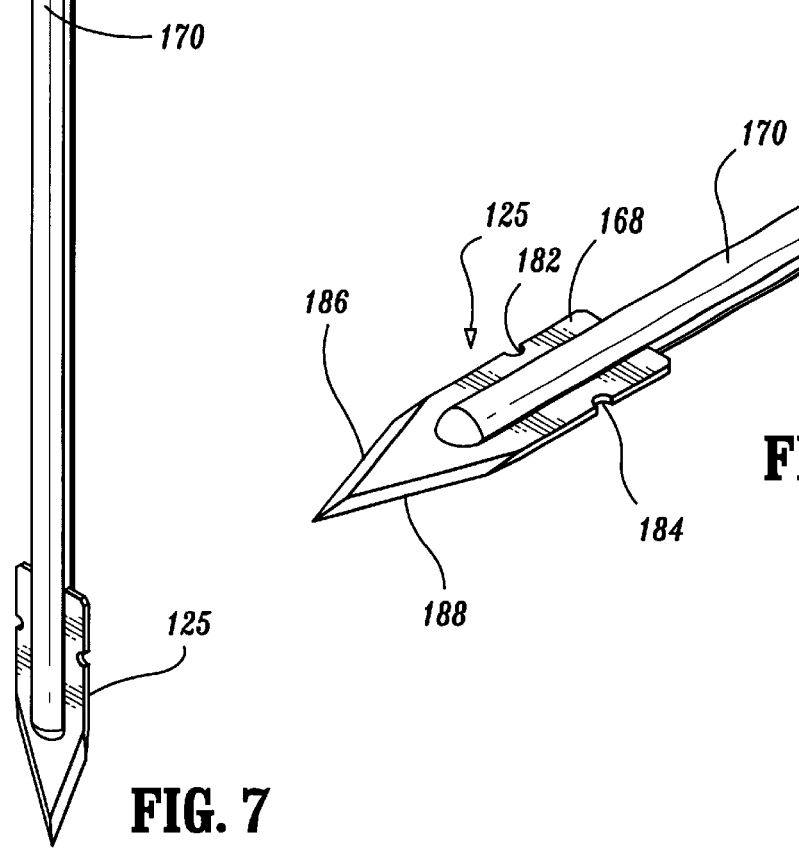
FIG. 9
FIG. 7

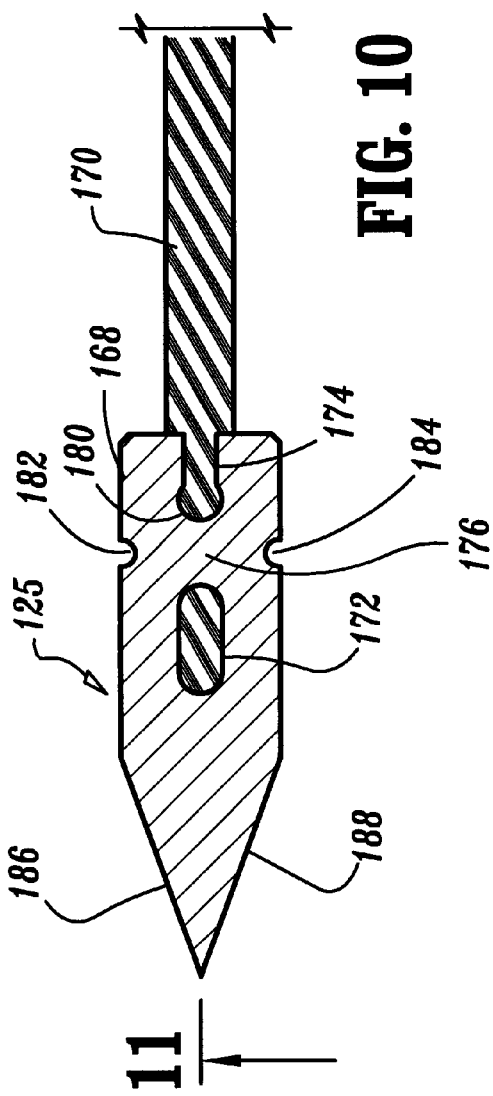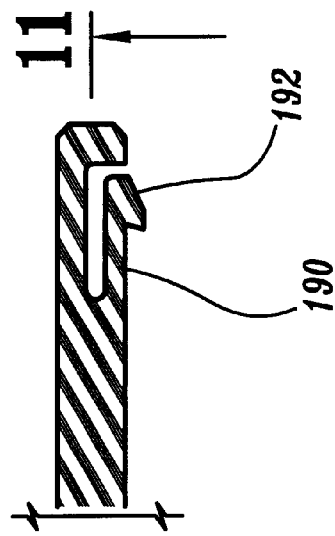
FIG. 10
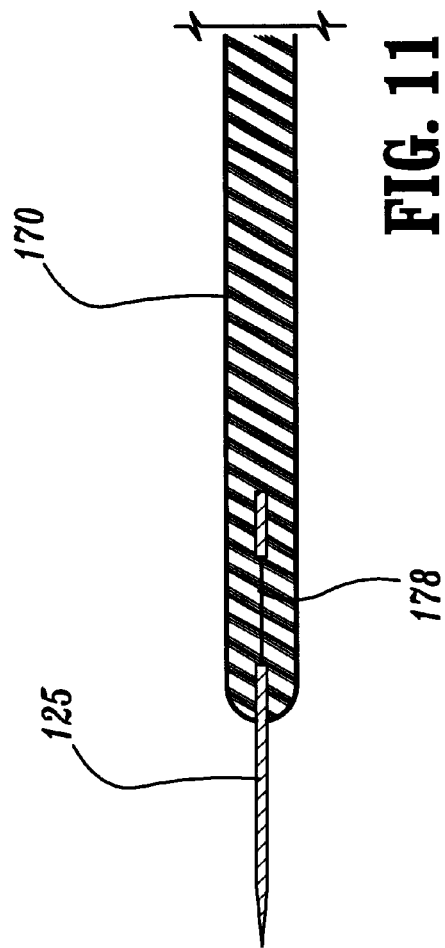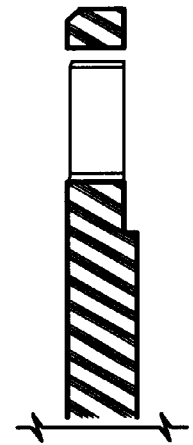
FIG. 11

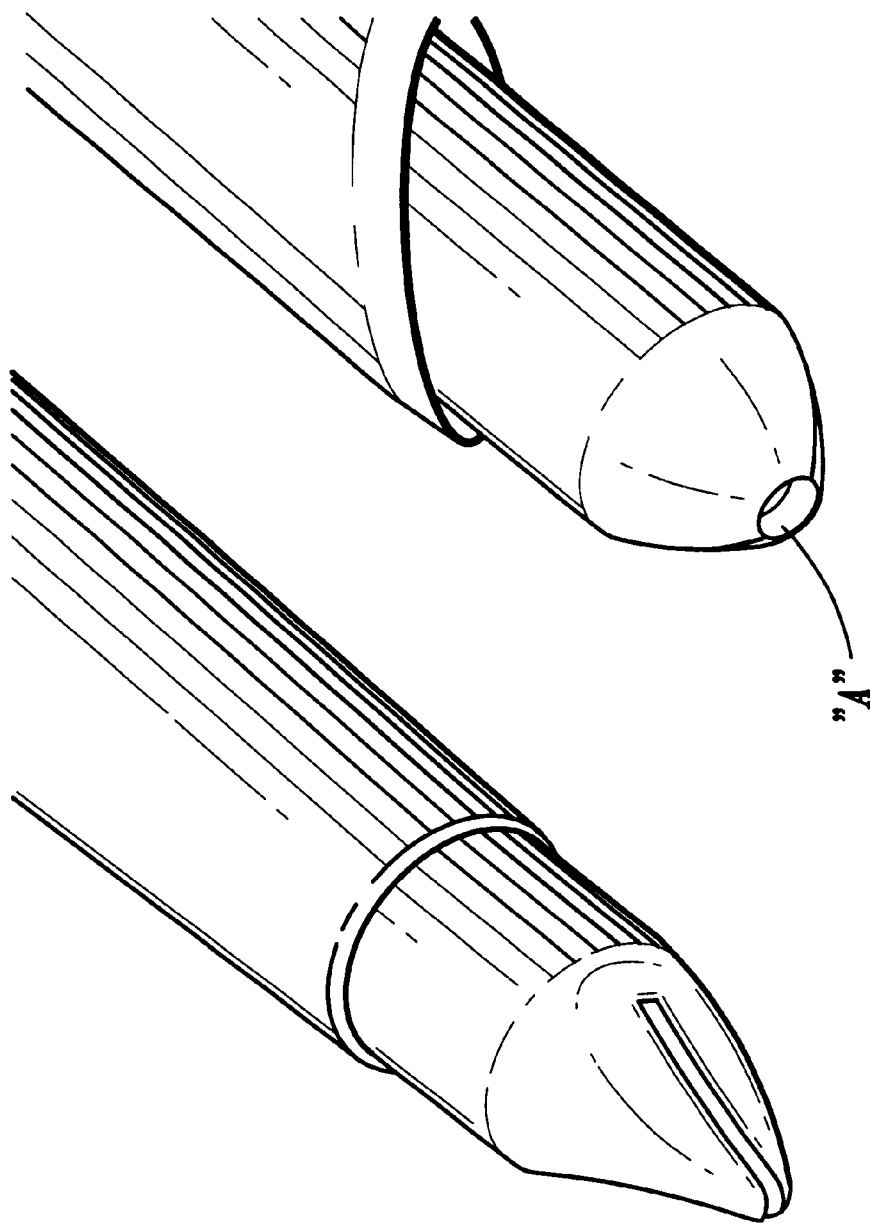

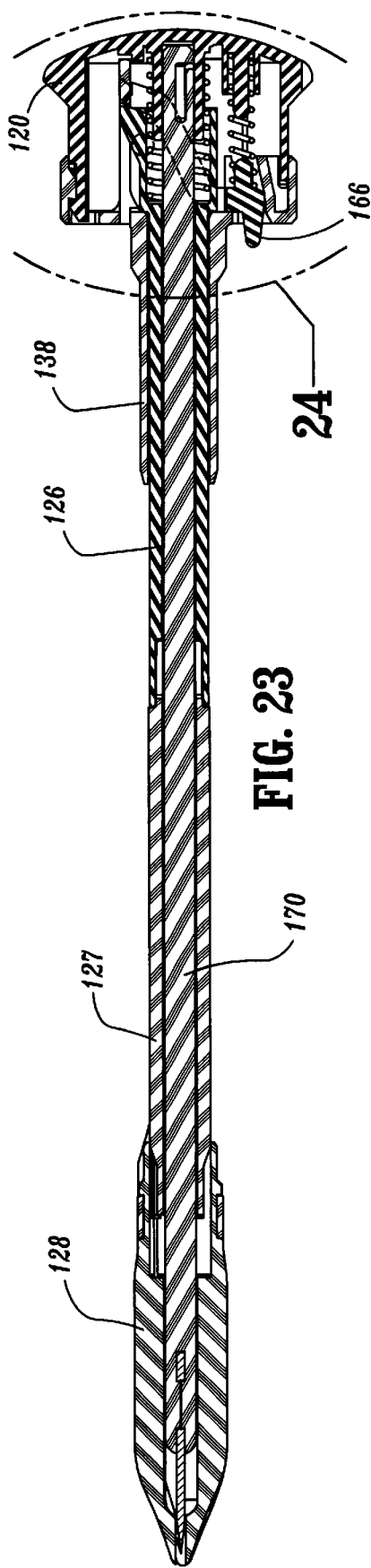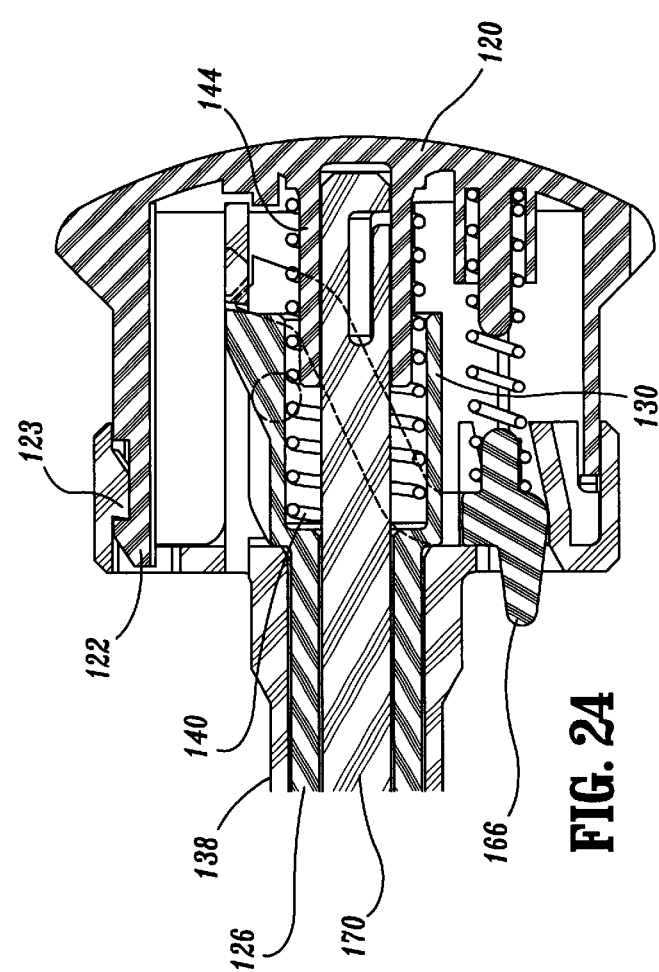

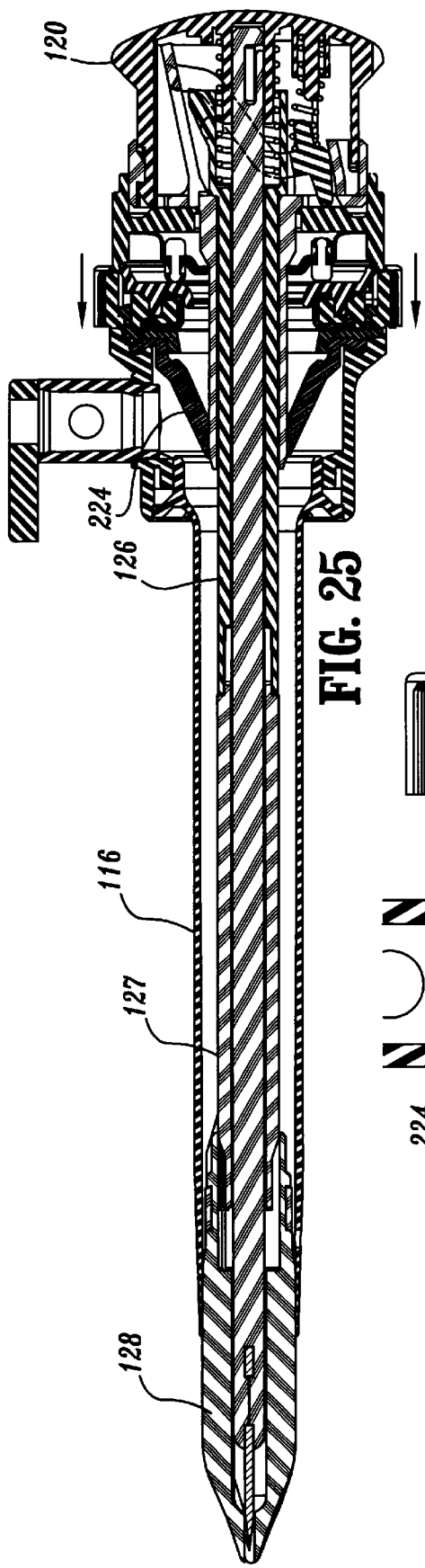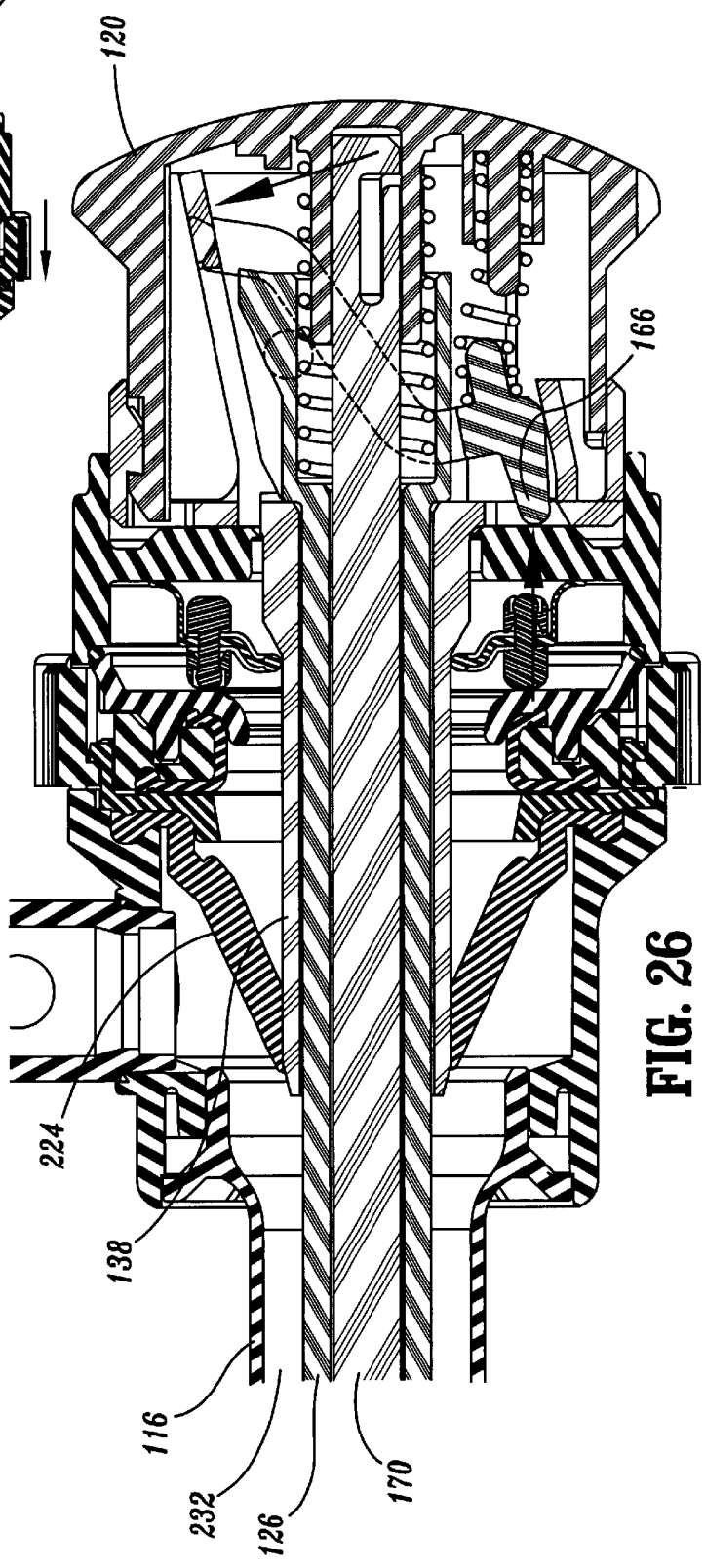

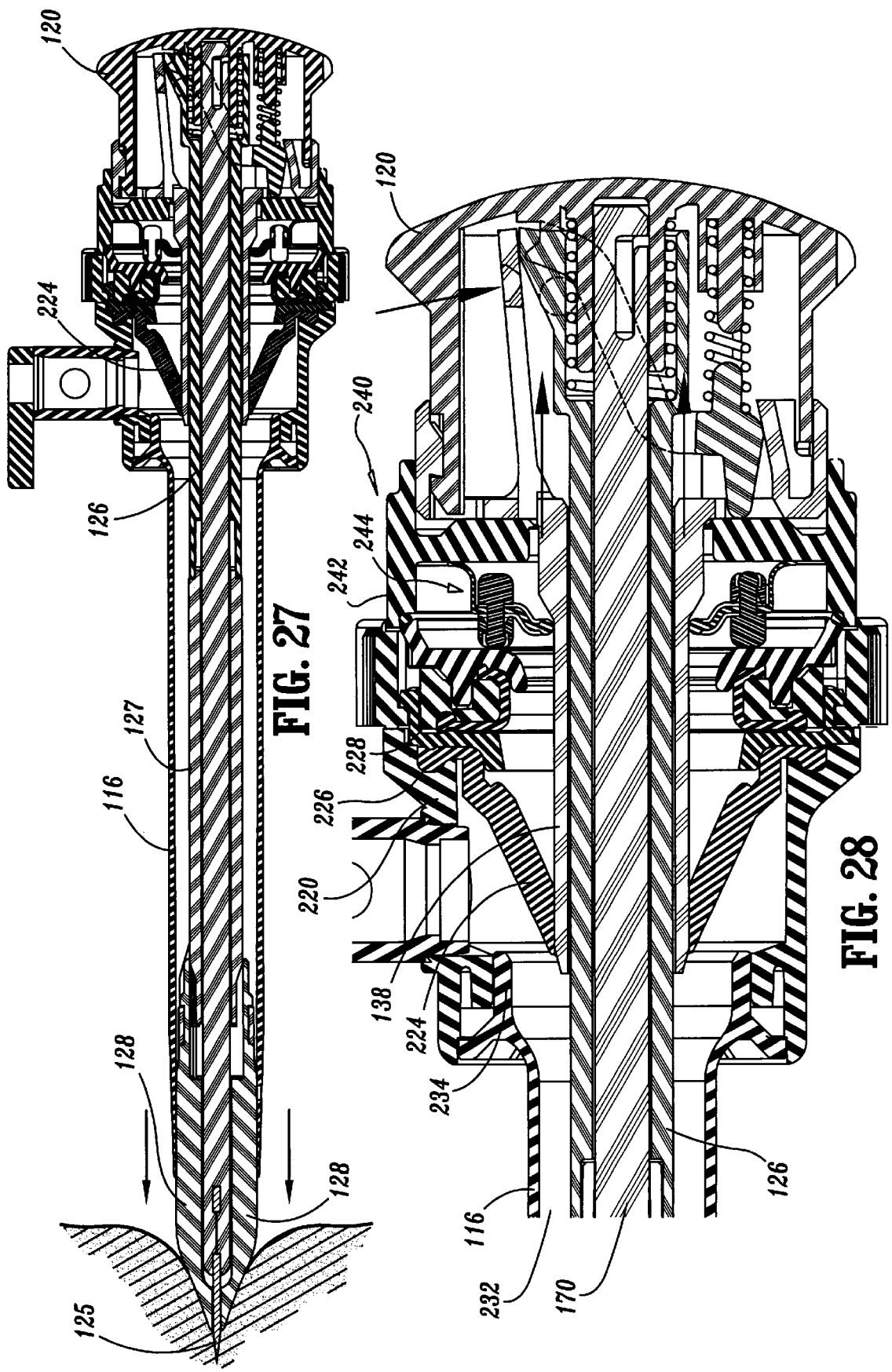

TROCAR SYSTEM AND METHOD OF USE

BACKGROUND

1. Technical Field

The present disclosure relates to trocar systems for inserting cannulas into patients, and more particularly to modular trocar systems and methods of assembly of trocar systems.

2. Background of Related Art

Minimally invasive procedures are continually increasing in number and variation. Forming a relatively small diameter temporary pathway to the surgical site is the key feature of most minimally invasive surgical procedures. The most common method of providing such a pathway is by inserting a trocar assembly through the skin. In many procedures the trocar is inserted into an insufflated body cavity of a patient. In such procedures, trocar assemblies with seal mechanisms are utilized to provide the necessary pathway to the surgical site while minimizing leakage of insufflation gases through the inserted cannula.

Trocar assemblies typically include an obturator removably inserted through a cannula assembly. The obturator is assembled with the cannula portion such that the obturator's sharp tip portion extends from a distal end opening of the cannula to facilitate insertion of the cannula through the body wall of the patient. Trocar assemblies are commonly provided with a safety shield of some fashion which protects against unintentional puncturing by the sharpened tip of the obturator. Mechanisms which control the relative movement and locking of the safety shield and the obturator's penetrating tip exist. Such mechanisms can be complex and often require numerous moving parts to accomplish the release and resetting of a the safety shield lock feature so as to permit the obturator's penetrating tip to function only when desired to facilitate insertion of the trocar assembly and placement of the cannula portion thereof.

A continuing need exists for novel trocar assemblies which provide safety shield latch mechanisms which require fewer component parts while providing increased reliability before, during and after insertion of the trocar assembly in a patient.

SUMMARY

The present disclosure provides a modular trocar system which overcomes disadvantages associated with previous trocar systems. The presently disclosed modular trocar system satisfies the need for more reliable trocar assemblies while improving manufacturing efficiencies.

In particular, the present disclosure provides trocar system including a cannula and an obturator assembly being at least partially insertable through the cannula. The obturator assembly including a housing, a penetrating tip disposed at a distal end, an elongated shield including a guard extending from a shaft are movable relative to the penetrating tip, and a latch mechanism disposed generally within the housing. The latch mechanism facilitates changing the configuration of the obturator assembly between a fixed-shield orientation, wherein at least a portion of the guard is maintained to extend at least partially distal of the penetrating tip to prevent puncturing of tissue by the penetrating tip, to a non-fixed shield orientation whereby upon application of force to the distal end of the obturator assembly, the guard and penetrating tip are permitted to move relative one another to facilitate puncturing of tissue by the penetrating tip.

BRIEF DESCRIPTION OF THE DRAWINGS

Various embodiments are described herein with reference to the drawings, wherein:

FIG. 1 is a perspective view of one embodiment of the modular trocar system constructed in accordance with the present disclosure;

FIG. 2 is a perspective view of an obturator assembly constructed in accordance with the present disclosure;

FIG. 4 is an enlarged perspective view of a latch mechanism for a safety shield of the obturator assembly of the embodiment of FIG. 2;

FIG. 5 is a perspective view of a shield member of the obturator assembly;

FIG. 6 is a perspective view of a slider member of the latch mechanism;

FIG. 7 is a perspective view of a knife assembly of the obturator assembly;

FIG. 8 is an enlarged view of the indicated area of detail in FIG. 7;

FIG. 9 is a perspective view of the distal end of the knife assembly of FIG. 7;

FIG. 10 is a horizontal cross-sectional view taken through the knife assembly of FIG. 7;

FIG. 11 is a cross-sectional view taken along section line 11—11 of FIG. 10;

FIG. 20A is a perspective view of the distal end portion of the trocar assembly of FIG. 1;

FIG. 20B is a perspective view of an existing trocar assembly design;

FIG. 23 is a longitudinal cross-sectional view taken through the obturator assembly;

FIG. 24 is an enlarged view of the indicated area of detail of FIG. 23;

FIG. 25 is a longitudinal cross-sectional view taken through the trocar assembly of the present disclosure;

FIG. 26 is an enlarged view of the proximal end components of FIG. 25;

FIG. 27 is view similar to FIG. 25, which shows insertion of a trocar assembly through the skin of a patient; and FIG. 28 is an enlarged view of the proximal end components of FIG. 27.

DETAILED DESCRIPTION OF PREFERRED EMBODIMENTS

Figure 3:
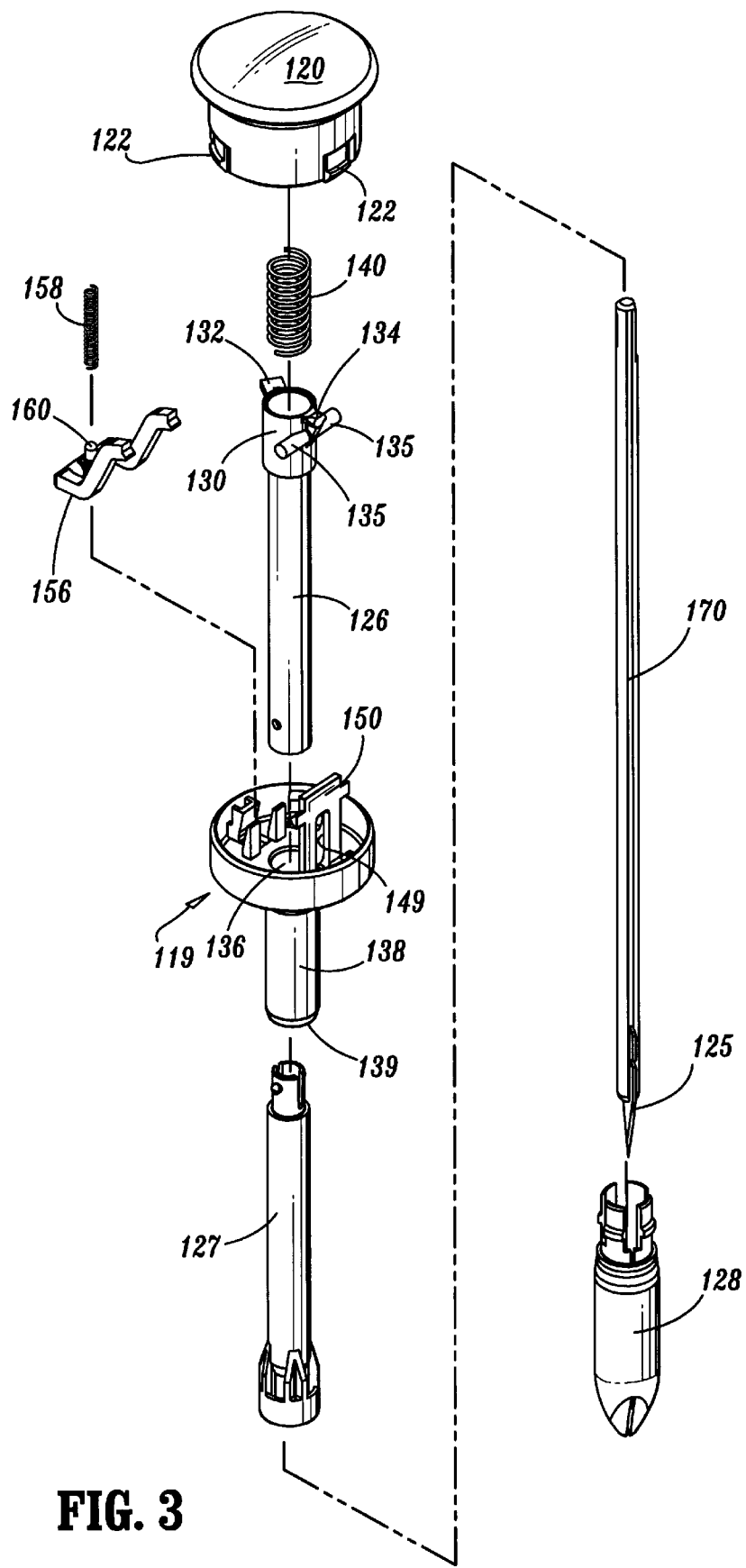
FIG. 3 is a perspective view with parts separated of the obturator assembly of the embodiment of FIG. 2.

Referring initially to FIGS. 1 and 2, one embodiment of a modular trocar system in accordance with the present disclosure is designated by reference numeral 100 throughout the several views. Modular trocar system 100 is particularly adapted for use in minimally invasive surgical procedures such as endoscopic or laparoscopic procedures. Generally, modular trocar system 100 includes two principal subassemblies, namely an obturator assembly 110 and a cannula assembly 112. Cannula assembly 112 includes a seal assembly 114 and a cannula 116, as described in detail further herein.

Except where noted otherwise, the materials utilized in the components of the presently disclosed modular trocar system generally include materials such as either ABS or polycarbonate for housing sections and related components and stainless steel for components that are required to cut tissue. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Referring now to FIGS. 3–9, and initially to FIGS. 3–6, obturator assembly 110 includes an obturator housing 118 formed from housing base 119 and cylindrical housing cover 120. Once the appropriate components are positioned therewithin (as described below), housing base 119 may be attached to cylindrical housing cover 120 by engaging mating surfaces, for example by resilient latches 122 formed on cover 120 interlocking with correspondingly shaped engaging surfaces 123 (FIG. 24) formed in the housing base 119. To uniformly connect base 119 and cover 120, preferably at least three corresponding latches 122 and engaging surfaces 123 are provided and are spaced evenly around the circumference of cover 120 and housing base 119, respectively. Base 119 and cover 120 are preferably molded from an ABS material and are preferably configured and dimensioned to functionally cooperate with various sizes of cannulas, e.g., 5–15 mm. Thus, obturator housing 118 is adapted to be a modular component for use with a wide range of trocar assemblies.

When fully assembled, obturator assembly 110 includes a safety shield assembly that is movable with respect to a penetrating tip such as, for example, knife blade 125. The safety shield assembly includes a shaft formed from an elongated hollow shield member 126 and a shield extension 127. A distal guard member 128 is attached to the distal end of shield extension 127. Preferably, all of the safety shield assembly components are molded from a polycarbonate material. Guard member 128 is preferably formed as a "dolphin nose" to help minimize the force necessary to penetrate the body. As shown in FIG. 5, the distal section of elongated shield member 126 is provided with a pair of opposing receiving holes 148 (only one is visible) to facilitate interaction with shield extension 127, as will be described below. Elongated shield member 126 also includes a proximal end portion such as collar 130 having a shield position indicator, such as indicator flag 132, extending transversely relative to elongated shield member 126. Preferably flag 132 is colored to contrast sharply with the surrounding housing components. For example, indicator flag 132 may be red if the surrounding housing components are white or light colored. Proximal end portion of collar 130 includes a bearing surface such as ledge 134 and a pair of posts 135 formed below ledge 134 and extending transversely outwardly.

Elongated shield member 126 is disposed within a longitudinal throughbore 136, FIG. 3, formed through cylindrical extended portion 138 of housing base 119 with a distal end surface of collar 130 abutting housing base 119 on a proximal face thereof. Cylindrical extended portion 138 may be molded as part of housing base 119 or molded separately and mounted to housing base 119, e.g., by sonic welding. Cylindrical extended portion 138 provides transverse support to the shield and obturator components that pass therethrough and preferably includes an inward taper 139 at its distal end to facilitate passage through valve/seal assemblies. Abutment between the distal and surface of collar 130 and housing base 119 limits distal movement of shield member 126 relative thereto. Ledge 134 interacts with a slot 149 formed in a latch member 150 molded as part of base 119 to assist in the angular orientation of shield member 126 relative to housing 118.

Figure 14:
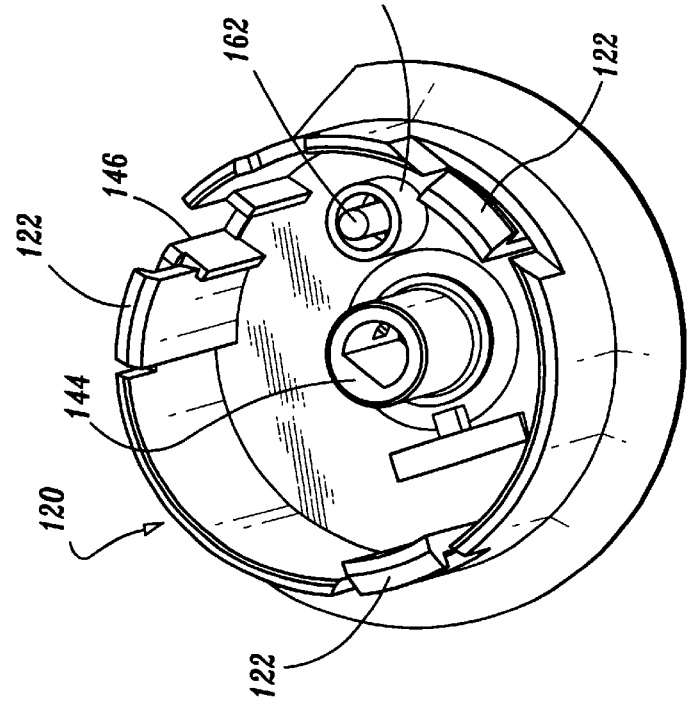
FIG. 14 is a perspective view of the inside of a housing cover of the obturator assembly.

The safety shield assembly further includes a coil spring 140 the distal end of which is seated in shield member 126 in an opening formed at the proximal end of collar 130. Referring temporarily to FIG. 14, housing cover 120 preferably includes a distally directed, hollow cylindrical post 144 molded to the proximal face thereof. Although hollow post 144 serves several functions, initially it is noted that coil spring 140, which biases shield member 126 toward a distal-most position is positioned around hollow cylindrical post 144. Thus, hollow post 144 assists in alignment of coil spring 140, e.g., to prevent kinking thereof. Referring temporarily to FIG. 24, the diameter of coil spring 140 is preferably selected so that spring 140 fits in a gap region between concentrically disposed collar 130 and hollow post 144.

Housing cover 120 is further provided with an open ended slot 146 (FIGS. 2 and 14) to slidable receive position indicator flag 132. Housing cover 120 may further be provided with indicia (not shown) positioned adjacent open ended slot 146 to provide additional visual indication to the user of the relative positioning of the shield, as is known in the art.

As noted above, the shield member 126 (and therefore the entire shield assembly) is biased in a distal-most position by coil spring 140. A latching mechanism is provided as part of obturator assembly 110 to prevent proximal movement of the shield assembly until such a time as obturator assembly 110 is inserted in a cannula assembly, e.g., cannula assembly 112, and the surgeon is prepared to begin trocar entry.

As best shown in FIGS. 4–6, the latching mechanism includes latch member 150 having two vertical leg portions 152 and 154 connected by a web portion 155. A pair of biasing posts 157, 159 extend outwardly, one for each side of latch member 150. Latch member 150 is preferably molded as part of housing base 119 in cantilevered fashion. However, latch 150 may be formed as a separate element and secured to base 119 by suitable known techniques.

A release member such as slider 156 is distally biased by a coil spring 158 which is maintained in axial alignment with a lower end of slider 156 by a post 160. The proximal end of coil spring 158 bears against the inner surface of housing cover 120 and is maintained in position between a post 162 and a cylindrical base 164 formed in housing cover 120 (FIG. 14). The distal biasing of slider 156 causes an arming button 166, which extends distally from the distal face of slider 156, to project through an opening formed in the housing base 119 (FIG. 24). Compression of obturator assembly 110 relative to cannula assembly 112 causes slider 156 to translate vertically in a proximal direction as will be described further herein. As shown in FIG. 6, slider 156 includes a pair of legs 156a, 156b which are each connected to a base portion 156c and terminate in a crook 156d, 156e configured and dimensioned to engage posts 157, 159 respectively, of latch 150.

In a preferred embodiment, the components described above, namely housing base 119, housing cover 120, the latching mechanism components, coil spring 140, cylindrical extended portion 138 and elongated shield member 126 constitute a first modular subassembly that may be advantageously manufactured in large quantities and inventoried for use across a wide range of trocar assembly sizes. As noted hereinbelow, other modular subassemblies may be manufactured to different size specifications, e.g., 5 mm, 10 mm, 15mm, but all would be functionally operable with the first modular subassembly disclosed herein.

Referring to FIGS. 3 and 7–11, assembly of a second modular subassembly including knife blade 125 will now be addressed in detail. Knife blade 125 is preferably fabricated from stainless steel by a suitable process, e.g., by stamping or metal injection molding.

A proximally extending elongated portion 168 is provided to facilitate attachment of knife blade 125 to a knife rod 170. Elongated proximal portion 168 is provided with a slot 172 and a notch 174. Preferably, knife rod 170 is formed by injection molding. Knife blade 125 is positioned in the injection mold such that when the rod material is injected into the mold, the material flows around a web portion 176, FIG. 10, which separates slot 172 and notch 174. When the material rejoins at slot 172, it forms a knit-line 178, FIG. 11, and attaches knife blade to the distal end of knife rod 170. Preferably, slot 174 is provided with an arcuate distal terminus 180 in the shape of a "cul de sac" to permit the rod material to flow outwardly and fill terminus 180. Knife blade 125 is further provided with a pair of lateral notches 182, 184 formed on either side of web portion 176. Notches 182, 184 facilitate proper orientation of knife blade 125 in the injection mold prior to formation of knife rod 170. Finally, knife blade 125 has a pair of sharpened cutting edges 186, 188, which converge to form a sharp penetration point.

Referring to FIGS. 7, 8, 10 and 11, knife rod 170 has a flexible finger 190 formed at a proximal end. Flexible finger 190 includes a cam surface 192 extending outwardly at a proximal end to facilitate assembly of knife rod 170 with housing cover 120, as will be described in greater detail herein.

Figure 13:
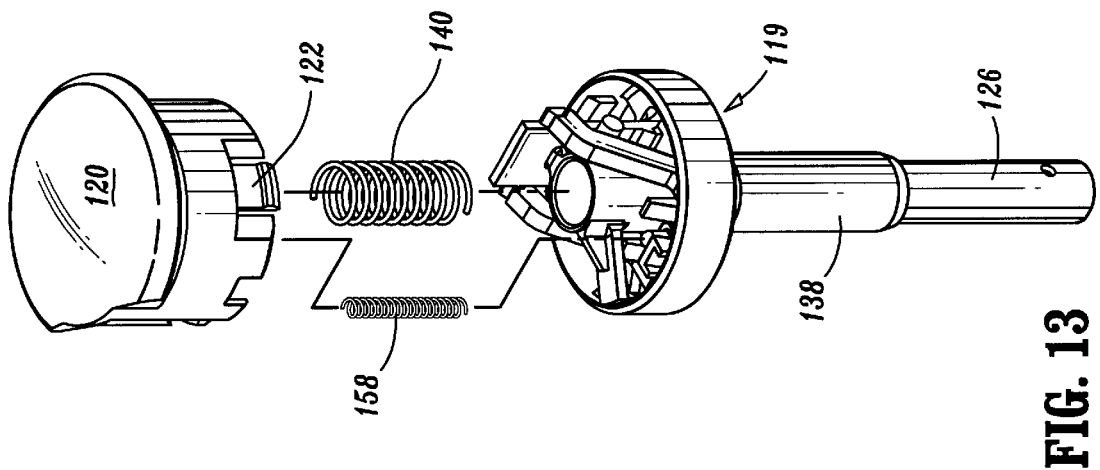
FIG. 13 is a further step of assembling the obturator assembly.
Figure 12:
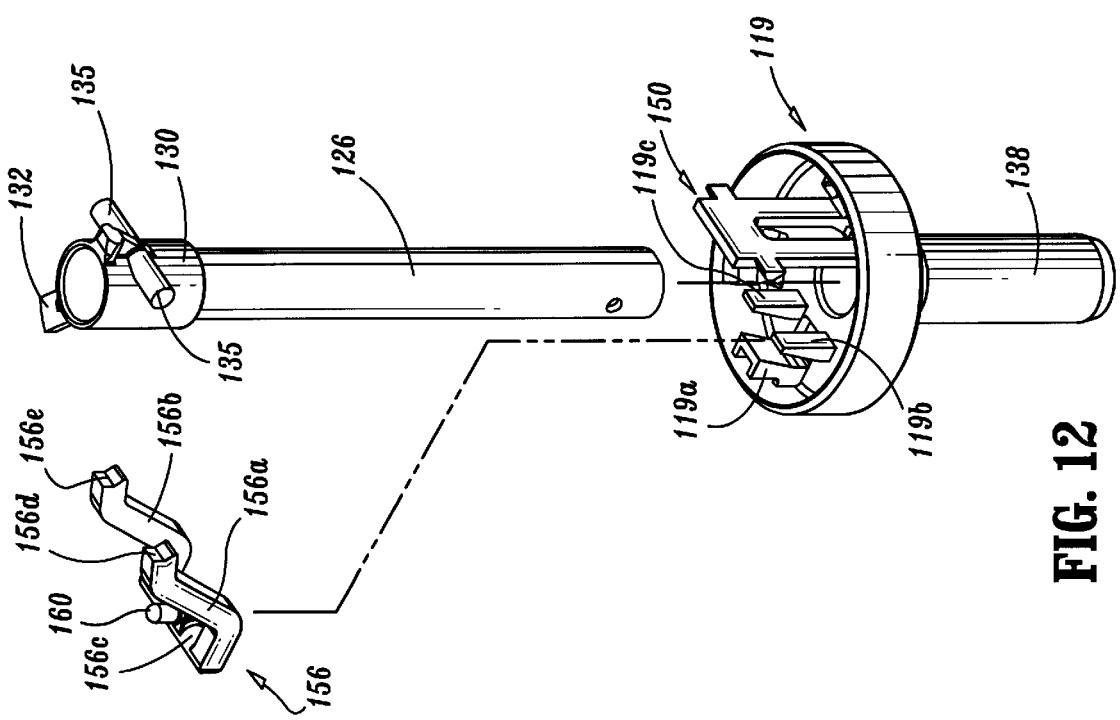
FIG. 12 is a perspective view illustrating a step of assembling the obturator assembly.
Figure 16:
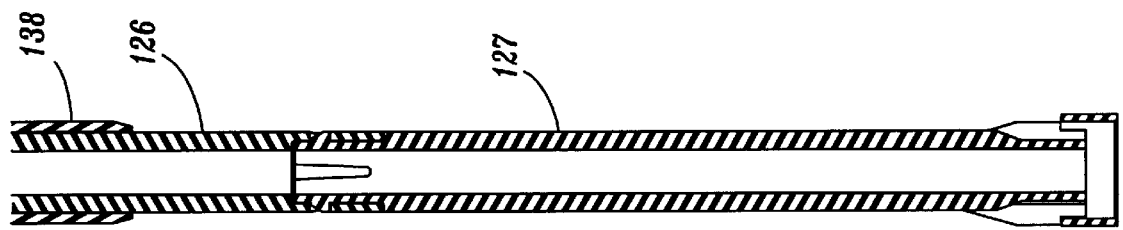
FIG. 16 is a longitudinal cross-sectional view illustrating the assembled shield member and a shield extension member.
Figure 15:
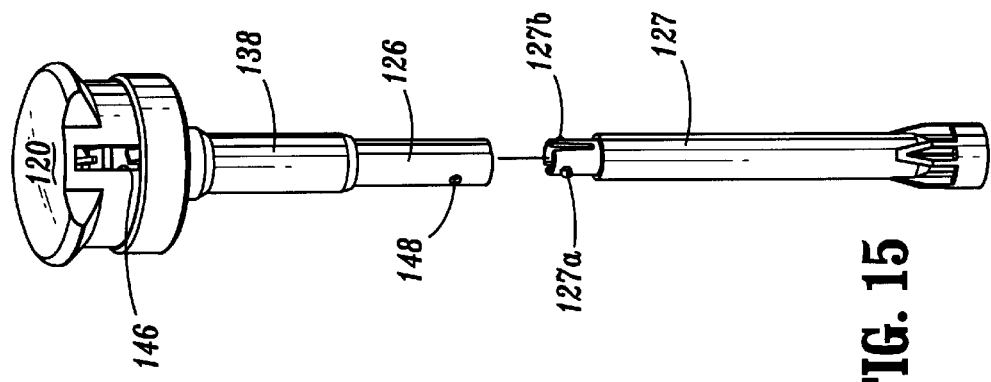
FIG. 15 is a further step in the method of assembling the obturator assembly.

Referring now to FIGS. 12–20, a novel method of assembly of obturator assembly 110 is disclosed. As shown in FIG. 12, shield member 126 and slider 156 are fit into base 119. Shield member 126 rides over slider 156 causing the slider's legs 156a, 156b to ride on top of posts 135 on shield member 126. Slider 156 fits over guide posts 119a, 119b and 119c such that base portion 156c is disposed between post 119a and posts 119b, 119c. Further, legs 156a, 156b are disposed on the outboard sides of posts 119b, 119c, respectively. Shield spring 140 and slider spring 158 are added, as shown in FIG. 13, and housing cover 120 is snapped in place as described above. Referring to FIGS. 15 and 16, shield extension 127 is then snapped into place at the distal end of slider 126. In particular, shield extension 127 has a clevis formed at a proximal end defining two flexible halves. A pair of nubs 127a, 127b snap fit into receiving holes 148 on shield member 126.

Figure 17:
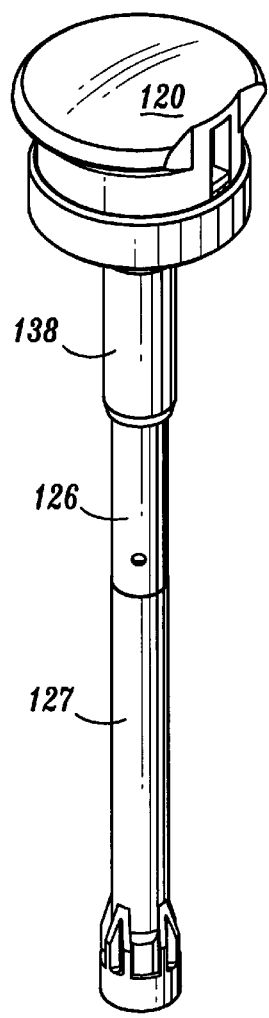
FIG. 17 is a further step illustrating the assembly of a knife rod with previously assembled components of the obturator assembly.
Figure 18:
FIG. 18 is a cross-sectional view of the proximal end of the components of the obturator assembly illustrated in FIG. 17.
Figure 19:
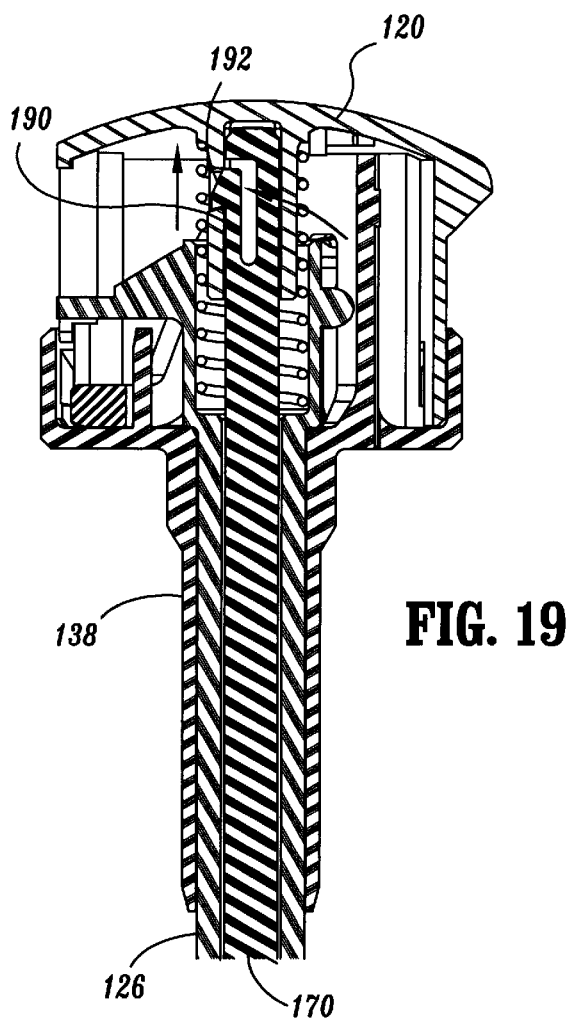
FIG. 19 is a view similar to FIG. 18, which illustrates securement of the knife rod within the housing cover.

Referring to FIGS. 17–19, knife rod 170 is slid in through the distal end of shield extension 127, through shield 126, and snapped in place in housing cover 120. As shown in FIGS. 18 and 19, insertion of knife rod 170 into hollow cylindrical post 144 of housing cover 120 causes cam surface to flex finger 190 until cam surface 192 is adjacent recess 193 formed in housing cover 120 whereby camming surface enters recess 193 to secure knife rod 170 in cover 120.

Figure 20:
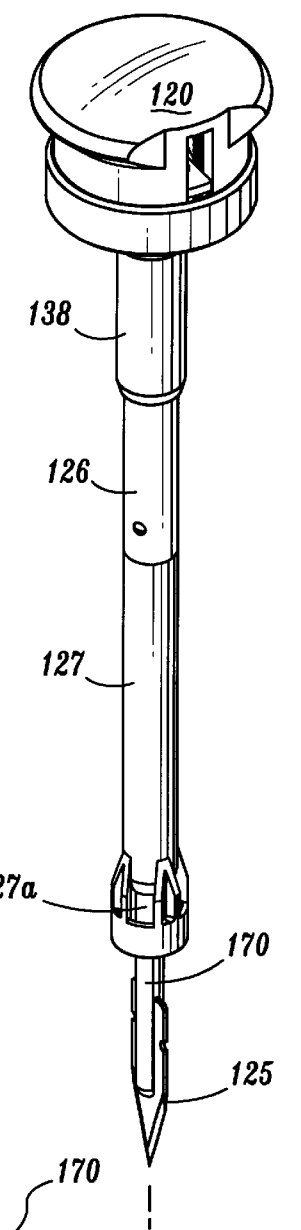
FIG. 20 is a perspective view illustrating assembly of a guard member with the shield extension member.
Figure 21:
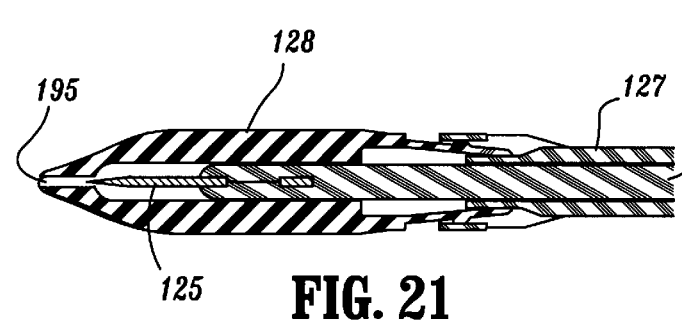
FIG. 21 is a longitudinal cross-sectional view taken through the distal end of the components illustrated in FIG. 20.
Figure 22:
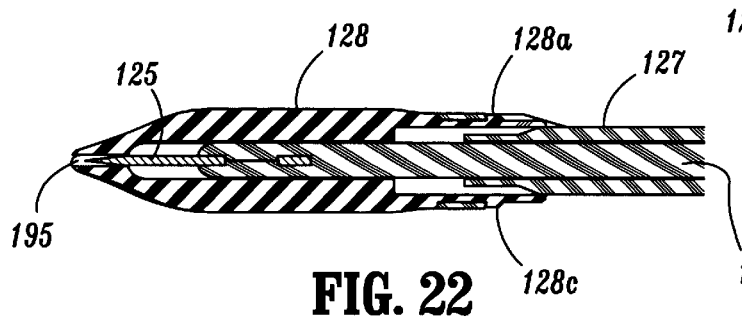
FIG. 22 is a view similar to FIG. 21, showing the guard element attached to the distal end of the shield extension member.

Referring to FIGS. 20–22, guard 128 is attached to distal end of shield extension 127. To facilitate attachment, guard 128 is provided with a series of flexible fingers 128a, 128b, 128c, 128d each having a raised portion formed thereon. The raised portions lock in place in openings such as opening 127a formed near the distal end of shield extension member 127. This unique method of assembly is particularly advantageous in that it allows for zero defects on the nose portion of guard 128 which translates into less hang up of the nose portion on tissue upon insertion of trocar assembly 100. For example, FIGS. 20A and 20B illustrate a comparison of the distal end portions of presently disclosed trocar assembly 100 and an existing trocar assembly design. The trocar design shown in FIG. 20B illustrates a circular opening labeled as "A" at the distal end. This opening enables a gap to exist between the knife blade and the opening upon initial insertion of the trocar assembly into a patient, thereby permitting hang-ups of the opening on tissue to occur. The presently disclosed trocar assembly 100 reduces the likelihood of such hang-ups by utilization of the "dolphin nose" design to eliminate the large gaps between the guard element and the knife blade. As an additional feature, either guard member 128 and/or knife blade 125 may be provided with a hydrophillic coating to further reduce the insertion force required to insert trocar assembly 100.

As shown in FIGS. 20–22, the geometries of and cooperation between knife blade 125 and guard member 128 facilitate ease of insertion of modular trocar system 100 through a patient's body wall while maintaining surgeon control and, by reason of spring biased guard 128, provide an enhanced margin of safety to internal organs. Cutting surfaces 186, 188 are extendable beyond the slot 195 formed in guard 128. The knife tip portion defines a planar triangular shape. The knife tip portion may initially be generally formed by stamping or metal injection molding and the cutting edges 186, 188 finely sharpened on both sides of knife blade 125, for example, by machining and/or polishing of the surfaces. Cutting surfaces 186, 188 preferably extend radially outwardly to just within the outer diameter of the cylindrical portion of guard member 128, thereby achieving an incision which approximates the diameter of guard member 128. By incising to the diameter of guard member 128, the force required for inserting modular trocar system 100 through tissue, such as the patient's abdominal wall, is reduced.

For larger diameter trocar assemblies, each of the components of obturator assembly 110 are the same except a larger sized knife blade and guard member are attached to knife rod 170. Also, a larger cannula is attached to the cannula body. This interchangeability of different sized knives and guard members with standard sized components located proximally thereof obviates the need to manufacture and inventory both the components and whole units of non-modular, conventional trocar systems. In particular, the more complex and, therefore, more expensive size-specific elements located in the obturator housing need not be manufactured and inventoried. The manufacturer or distributor need only assemble the appropriate sized knife and guard member with the otherwise standard sized control components as demand dictates.

Referring now to FIGS. 1 in conjunction with and 25–28, cannula assembly 112 of modular trocar system 100 includes a molded cylindrical base portion 216 having transversely extending grip portions 218 formed to extend form an annular flange formed at the proximal end of cylindrical base 216. A series of slots 222 are formed along the underside or distal side of grips 218. A similar modular cannula assembly is disclosed in U.S. Pat. No. 5,807,338 to Smith et al., the entire contents of which are hereby incorporated by reference. It is also contemplated, that either cannula base portion 216 or cannula 116 or both may be formed of transparent or translucent material.

Slots 222 are particularly advantageous in two respects. First, in assembling cannula assembly 112, there are three basic principle components: cylindrical base portion 216 having outwardly directing finger grips 218, a duck bill valve element 224 having a flange 226 which is configured and dimensioned to rest on annular flange 220 of cylindrical base portion 216 and a cannula housing cover portion such as proximal housing element 228 which is configured and dimensioned to rest on duck bill flange 226 and within the outwardly directed finger grips 218. It has been found that by coring out the underside of outwardly extending finger grips 218 with parallel slots 222, molding sinks which had been previously forming on the proximal side of outwardly extending fingers 218 of cylindrical base portion 216 were significantly reduced, thereby providing a much more reliable flat surface, as best shown in FIG. 18, against which duck bill flange 226 may rest and against which the upper or proximal housing element 228 may be welded.

This greater cooperation between the two cannula housing elements reduces the force which must be applied as between the two housing elements during the welding process, thereby reducing the likelihood that the duck bill valve 224 will be torqued. Torquing of the duck bill valve 224 can potentially reduce the sealing function of the element in the absence of a surgical instrument inserted therethrough.

The second respect in which slots 222 are advantageous is that on the underside of the cylindrical base portion 216 is normally the place where the user grips the cannula the cylindrical base portion 216. Accordingly, the slots provide an improved gripping surface to the user.

A further feature of cannula assembly 112 is the provision of a detachable cannula 116 which readily connects and disconnects from cylindrical base portion 216. Cannula 116 is preferably molded with a substantially constant inner and outer diameter. However, cannula 116 preferably includes a slightly larger inner diameter at its proximal end, e.g., of 2–3 cms length, to facilitate introduction of instrumentation, and a tapered outer diameter at its distal-most portion, e.g. over the distal-most 2–3 cms of length, the tapered outer diameter being largest at a proximal end thereof and smallest at a distal end thereof. In this way, molding is facilitated while penetration force is minimized by reducing the outer diameter of cannula 116 in the region where tissue first makes contact and by providing a gradual taper to the outside diameter to assist in dilation of tissue as it passes proximally along the outer wall of cannula 116.

An elastomeric O-ring may be interposed between cylindrical base portion 216 and cannula 116 to maintain a fluid-type seal between cannula 116 and cylindrical base portion 216. Cannula 116 is formed of a predetermined diameter so as to form a longitudinal throughbore 232 in communication with a passageway formed through cylindrical base portion 216 and proximal housing element 228. Cannula 116 is further provided with an annular flange 234 which is particularly sized to be received in the distal end of cylindrical base portion 216. Flange 234 is preferably a standard size such that cannulas having different sized diameter passageways formed therethrough may be formed with a flange that has the same configuration and dimension as flange 234. In this manner, cannulas of varying sized and dimensions may be interchangeably attached to a given cylindrical base portion such as cylindrical base portion 216.

To facilitate the interconnectability of cannula 116 and cylindrical base portion 216, a quick connect mechanism is provided which, for example, may be by a series of engageable mating members (not shown) formed on cannula 116 proximal of flange 234 which interconnect cannula 116 with cylindrical base portion 216 by way of a series of mating indented surfaces (not shown) formed along the inner wall of cylindrical base portion 216. The two elements are brought into engagement with each other by inserting the proximal end of cannula 116 into the distal end of cylindrical base portion 216 and rotating cannula 116 clockwise until the mating members engage and lock into the mating surfaces. The two elements may be disengaged by applying a proximally directed force to the cannula toward cylindrical base portion 216 and rotating cannula 116 counterclockwise. This feature is particularly advantageous during manufacture and assembly of cannula assembly 112 in that it facilitates inventory management and manufacturing efficiencies due to the cylindrical base portion 216 now being a single component which is able to be utilized across multiple cannula diameter products, the only difference being the cannula which is ultimately secured to the cylindrical base portions at the final stage of manufacture.

Also provided on cannula assembly 112 is a seal assembly 240 which generally includes a housing 242 and a seal member 244. A similar seal assembly is disclosed in copending PCT Application Serial No. PCT/US98/08970 filed May 1, 1998 by Racenet et al., the entire contents of which are hereby incorporated by reference.

As another feature, cannula assembly 112 may be provided with suture anchoring structure, for example suture anchor holes 219 on finger grips 218 or devises 221 formed near the proximal end of cannula 116.

In usage, as shown in FIGS. 25–28, obturator assembly 110 is inserted in the proximal end of cannula assembly 112. Obturator assembly 110 is pushed into cannula assembly 112 until the bottom of housing body 119 contacts the proximal end of cannula assembly 112. In this manner, arming button 166 of slider 156 is forced into housing body 119 thereby causing slider 156 to rotate such that legs 156a and 156b push latch 150 outwardly so that web portion 155 is out of axial alignment with ledge 134, as best shown in FIGS. 25 and 26. Thereafter, trocar assembly 100 is inserted through the body wall of the patient, FIG. 27, causing the guard member 128 to be urged proximally to reveal knife blade 125. The proximal movement of guard member 128 and shield member 126 connected thereto by shield extension 127 causes legs 156a, 156b to be rotated back inwardly by posts 135. This motion pushes legs 156a, 156b upwardly and inwardly away from latch 150 so that crooks 156d, 156e, respectively, of slider 156 no longer bias latch 150, permitting latch 150 to rest against the outer surface of ledge 134. Once the knife blade 125 and distal portion of guard member 128 pass through the body wall of the patient, the force of spring 140 causes slider 126 to move distally, thereby resetting guard member 128 by way of ledge 134 once again blocking proximal movement of guard member 128. Once guard member 128 has returned to its distal (guarded) position, it cannot be retracted again until arming button 166 is permitted to return to its distal position, i.e., by releasing pressure from obturator assembly 110 to allow obturator assembly 110 to separate slightly from cannula assembly 112. Once this happens, spring 158 pushes slider 156 distally to permit legs 156a, 156b to re-engage posts 157, 159 of latch 150.

It will be understood that various modifications may be made to the embodiments disclosed herein. Therefore, the above description should not be construed as limiting, but merely as exemplifications of preferred embodiments. Those skilled in the art will envision other modifications within the scope and spirit of the present disclosure.

What is claimed is:

1. A trocar system which comprises:
    a cannula forming an opening longitudinally therethrough and having a proximally facing surface disposed near a proximal end thereof; and
    an obturator assembly including a shaft fixed relative to the housing and being at least partially insertable through the cannula and including:
        a housing disposed at a proximal end, the housing including a base portion having a distally facing end surface configured and dimensioned to facilitate close proximate positioning thereof with the proximally facing surface of the cannula;
        a penetrating tip comprising a flat knife blade secured to the shaft being disposed at a distal end;
        an elongated shield including a guard extending from a shaft, the penetrating tip and guard being movable relative one another; and
        a latch mechanism disposed generally within the housing, which facilitates changing the configuration of the obturator assembly between a fixed-shield orientation, wherein at least a portion of the guard is maintained to extend at least partially distal of the penetrating tip to prevent puncturing of tissue by the penetrating tip, to a non-fixed shield orientation whereby upon application of force to the distal end of the obturator assembly, the guard and penetrating tip are permitting to move relative one another to facilitate puncturing of tissue of the penetrating tip, the latch mechanism including;
        a release member having a button portion and camming surface; and
        a latch operatively associated with the release member, the latch having a blocking surface and a mating surface, the mating surface cooperating with the camming surface of the release member such that upon movement of the release member the camming surface biases the mating surface to move the latch such that the blocking surface permits axial movement of the shield.

2. A trocar system as recited in claim 1 wherein movement of the release member causes the blocking surface to be displaced out of axial alignment with the shield.

3. A trocar system as recited in claim 2 wherein the blocking surface is disposed proximal of the at least a portion of the shield.

4. A trocar system as recited in claim 1 wherein the button portion protrudes at least partially through an opening formed in the distally facing end surface of the obturator housing.

5. A trocar system as recited in claim 1 wherein the latch is biased such that the blocking surface is normally disposed in axial alignment with at least a portion of the shield to prevent axial movement thereof.

6. A trocar system as recited in claim 1 wherein the release member is configured and dimensioned such that axial movement of the release member imparts lateral movement of the blocking surface of the latch member.

7. A trocar system as recited in claim 1 wherein the shield includes an extended surface which is disposed on the shield such that upon axial movement of the shield, the extended surface biases the actuator member away from the latch to permit the latch to return to its original orientation.

8. A trocar system as recited in claim 1 wherein the guard is configured and dimensioned to completely enclose the penetrating tip.

9. A trocar system as recited in claim 1, wherein the shield and guard are separate elements fitted together during assembly of the obturator.

* * * * *